US008740818B2

(12) United States Patent
Walker et al.

(10) Patent No.: US 8,740,818 B2
(45) Date of Patent: Jun. 3, 2014

(54) METHOD AND APPARATUS FOR CHARACTERIZATION OF CLOT FORMATION

(75) Inventors: William F. Walker, Earlysville, VA (US); Michael B. Lawrence, Charlottesville, VA (US); Francesco Viola, Charlottesville, VA (US); Margaret Kramer Sande, Denver, CO (US)

(73) Assignee: Hemosonics, LLC, Charlottesville, VA (US)

( * ) Notice: Subject to any disclaimer, the term of this patent is extended or adjusted under 35 U.S.C. 154(b) by 631 days.

(21) Appl. No.: 12/909,600

(22) Filed: Oct. 21, 2010

(65) Prior Publication Data

US 2011/0034805 A1 Feb. 10, 2011

Related U.S. Application Data

(62) Division of application No. 10/971,178, filed on Oct. 22, 2004, now Pat. No. 7,892,188.

(60) Provisional application No. 60/513,264, filed on Oct. 22, 2003.

(51) Int. Cl.
*A61B 5/103* (2006.01)
*A61B 5/117* (2006.01)
*A61B 8/00* (2006.01)
*A61B 5/00* (2006.01)
*A61B 19/00* (2006.01)

(52) U.S. Cl.
USPC ............ 600/587; 600/438; 600/552; 600/553

(58) Field of Classification Search
USPC ......... 600/407, 437, 438, 443, 448, 552, 553, 600/587, 595
See application file for complete search history.

(56) References Cited

U.S. PATENT DOCUMENTS 4,112,740 A 9/1978 Brandestini
(Continued)

FOREIGN PATENT DOCUMENTS

WO 2011035162 3/2011

OTHER PUBLICATIONS

Amukele, et al., "Comparison of plasma with whole blood prothrombin time and fibrinogen on the same instrument," American Journal of Clinical Pathology, vol. 133, No. 4, Apr. 2010, pp. 550-556.
(Continued)

*Primary Examiner* — Max Hindenburg
*Assistant Examiner* — Adam Eiseman
(74) *Attorney, Agent, or Firm* — Meunier Carlin & Curfman LLC

(57) ABSTRACT

Methods, apparatus and systems for characterizing changes in at least one physical property of soft tissue. A series of acoustic pulses is generated and directed into the soft tissue such that at least one of the pulses is of sufficiently high intensity to induce physical displacement of the tissue. Waves reflected off the tissue, or a flexible member that moves with the tissue, are received and measured to estimate at least one characteristic of the physical displacement induced thereby. Repetition of the generating, receiving and estimating steps provides characterization of the at least one physical property over time. Methods, apparatus and systems for characterizing at least one physical property of blood, by generating a series of acoustic pulses and directing the series of pulses into the blood such that at least one of the pulses is of sufficiently high intensity to induce physical displacement of the blood. Acoustic pulses and/or optical waves reflected from the blood, or a flexible member in contact with the blood that moves with the blood, are received and measured to estimate at least one characteristic of the physical displacement induced thereby.

37 Claims, 7 Drawing Sheets

(56) References Cited

U.S. PATENT DOCUMENTS

| | | | |
|---|---|---|---|
| 4,558,589 A | 12/1985 | Hemmes et al. | |
| 4,695,956 A | 9/1987 | Leveen et al. | |
| 4,705,756 A | 11/1987 | Spillert et al. | |
| 4,814,247 A | 3/1989 | Spillert et al. | |
| 4,852,577 A | 8/1989 | Smith et al. | |
| 4,900,679 A | 2/1990 | Spillert et al. | |
| 5,056,357 A | 10/1991 | Dymling et al. | |
| 5,104,975 A | 4/1992 | McCormick et al. | |
| 5,205,159 A | 4/1993 | Carr et al. | |
| 5,234,839 A | 8/1993 | McCormick et al. | |
| 5,273,517 A | 12/1993 | Barone et al. | |
| 5,311,908 A | 5/1994 | Barone et al. | |
| 5,331,964 A | 7/1994 | Trahey et al. | |
| 5,473,536 A | 12/1995 | Wimmer | |
| 5,487,387 A | 1/1996 | Trahey et al. | |
| RE35,171 E | 3/1996 | McCormick et al. | |
| 5,605,154 A | 2/1997 | Ries et al. | |
| 5,606,971 A | 3/1997 | Sarvazyan | |
| 5,655,535 A | 8/1997 | Friemel et al. | |
| 5,657,760 A | 8/1997 | Ying et al. | |
| 5,673,699 A | 10/1997 | Trahey et al. | |
| 5,744,898 A | 4/1998 | Smith et al. | |
| 5,810,731 A | 9/1998 | Sarvazyan et al. | |
| 5,854,423 A | 12/1998 | Venegas | |
| 5,899,861 A | 5/1999 | Friemel et al. | |
| 5,921,928 A | 7/1999 | Greenleaf et al. | |
| 6,039,691 A | 3/2000 | Walker et al. | |
| 6,083,159 A | 7/2000 | Driscoll et al. | |
| 6,114,135 A | 9/2000 | Goldstein | |
| 6,117,081 A | 9/2000 | Jago et al. | |
| 6,135,957 A | 10/2000 | Cohen et al. | |
| 6,213,950 B1 | 4/2001 | Cespedes et al. | |
| RE37,171 E | 5/2001 | Busche et al. | |
| 6,225,126 B1 | 5/2001 | Cohen et al. | |
| 6,264,609 B1 | 7/2001 | Herrington et al. | |
| 6,270,459 B1 | 8/2001 | Konofagou et al. | |
| 6,277,074 B1 | 8/2001 | Chaturvedi et al. | |
| 6,283,917 B1 | 9/2001 | Jago et al. | |
| 6,371,912 B1 | 4/2002 | Nightingale et al. | |
| 6,402,704 B1 | 6/2002 | McMorrow | |
| 6,454,714 B1 | 9/2002 | Ng et al. | |
| 6,494,834 B2 | 12/2002 | Konofagou et al. | |
| 6,508,768 B1 | 1/2003 | Hall et al. | |
| 6,514,204 B2 | 2/2003 | Alam et al. | |
| 6,535,835 B1 | 3/2003 | Rubin et al. | |
| 6,537,819 B2 | 3/2003 | Cohen et al. | |
| 6,573,104 B2 | 6/2003 | Carr et al. | |
| 6,613,573 B1 | 9/2003 | Cohen | |
| 6,632,678 B2 | 10/2003 | Aiken et al. | |
| 6,685,646 B2 | 2/2004 | Cespedes et al. | |
| 6,687,625 B2 | 2/2004 | Srinivasan et al. | |
| 6,692,439 B1 | 2/2004 | Walker et al. | |
| 6,716,168 B2 | 4/2004 | Nock et al. | |
| 6,726,629 B1 | 4/2004 | Frinking et al. | |
| 6,764,448 B2 | 7/2004 | Trahey et al. | |
| 6,787,363 B2 | 9/2004 | Cohen et al. | |
| 6,797,519 B2 | 9/2004 | Cohen et al. | |
| 6,890,299 B2 | 5/2005 | Cohen et al. | |
| 6,951,544 B2 | 10/2005 | Trahey et al. | |
| 7,179,652 B2 | 2/2007 | Cohen et al. | |
| 7,192,726 B1 | 3/2007 | Carr et al. | |
| 7,202,048 B2 | 4/2007 | Carr, Jr. | |
| 7,207,939 B2 | 4/2007 | Husher | |
| 7,261,861 B2 | 8/2007 | Kautzky | |
| 7,374,538 B2 | 5/2008 | Nightingale et al. | |
| 7,399,637 B2 | 7/2008 | Wright et al. | |
| 7,422,905 B2 | 9/2008 | Clague et al. | |
| 7,439,069 B2 | 10/2008 | Nippoldt et al. | |
| 7,524,670 B2 | 4/2009 | Cohen et al. | |
| 7,732,213 B2 | 6/2010 | Cohen et al. | |
| 7,912,661 B2 | 3/2011 | Zeng et al. | |
| 7,972,271 B2 | 7/2011 | Johnson et al. | |
| 8,058,023 B2 | 11/2011 | Gurbel | |
| 2002/0013530 A1 | 1/2002 | Cespedes et al. | |
| 2002/0040187 A1 | 4/2002 | Alam et al. | |
| 2003/0013958 A1 | 1/2003 | Govari et al. | |
| 2003/0073244 A1 | 4/2003 | Cohen et al. | |
| 2003/0105398 A1 | 6/2003 | Vitek | |
| 2003/0171676 A1 | 9/2003 | Trahey et al. | |
| 2003/0204141 A1 | 10/2003 | Nock et al. | |
| 2004/0068184 A1 | 4/2004 | Trahey et al. | |
| 2004/0167403 A1 | 8/2004 | Nightingale et al. | |
| 2005/0004463 A1 | 1/2005 | Chen et al. | |
| 2005/0015001 A1 | 1/2005 | Lee et al. | |
| 2005/0053305 A1 | 3/2005 | Li et al. | |
| 2005/0148899 A1 | 7/2005 | Walker et al. | |
| 2007/0038095 A1 | 2/2007 | Greenleaf et al. | |
| 2007/0059840 A1 | 3/2007 | Cohen et al. | |
| 2007/0184508 A1 | 8/2007 | Cohen et al. | |
| 2007/0276236 A1 | 11/2007 | Jong | |
| 2008/0038828 A1 | 2/2008 | Cohen et al. | |
| 2008/0249408 A1 | 10/2008 | Palmeri et al. | |
| 2008/0261261 A1 | 10/2008 | Grimes et al. | |
| 2009/0112483 A1 | 4/2009 | Cohen | |
| 2011/0151491 A1 | 6/2011 | Dennis et al. | |
| 2012/0252127 A1 | 10/2012 | Gregor et al. | |

OTHER PUBLICATIONS

Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.

Anderson, "Preventing Deep Vein Thrombosis and Pulmonary Embolism," Center for Outcomes Research, U Mass Med Center, 1998, 23 pages.

Becker, R., "Cell-based models of coagulation: a paradigm in evolution," Journal of Thrombosis and Thrombolysis, vol. 20, No. 1, Aug. 2005, pp. 65-68.

Bercoff et al., "In vivo breast tumor detection using transient elastography," Ultrasound in Medicine & Biology, vol. 29, No. 10, 2003, pp. 1387-1396.

Bercoff, et al., "Supersonic Shear Imaging: a New Technique for Soft Tissue Elasticity Mapping," IEEE Transactions on Ultrasonics Ferroelectrics & Frequency Control, vol. 51, No. 4, 2004, pp. 396-409.

Bilgen, et al., "Error analysis in acoustic elastography. II. Strain estimation and SNR analysis", Journal of the Acoustical Society of America, vol. 101, 1997, pp. 1147-1154.

Bohs, et al., "A Real Time System for Quantifying and Displaying Two-Dimensional Velocities using Ultrasound," Ultrasound in Medicine & Biology, vol. 19, No. 9, Jul. 1993, pp. 751-761.

Bonnefous, et al., "Time Domain Formulation of Pulse-Doppler Ultrasound and Blood Velocity Estimation by Cross Correlation," Ultrasonic Imaging 8, 1986, pp. 73-85.

Brock, et al., "Assessing Thrombin Generation at the Point of Care," Clinical Chemistry, vol. 55, No. 3, Mar. 2009, pp. 398-399.

Carr, M., "In vitro assessment of platelet function," Transfusion of Medicine Reviews, vol. 11, No. 2, Apr. 1997, pp. 106-115.

Carroll, et al., "Measurement of functional fibrinogen levels using the Thrombelastograph," Journal of Clinical Anesthesia, vol. 20, No. 3, May 2008, pp. 186-190.

Carter, G., "Coherence and time delay estimation," Proc IEEE, vol. 75, No. 2, 1987, pp. 236-255.

Chakroun et al., "The influence of fibrin polymerization and platelet-mediated contractile forces on citrated whole blood thromboelastography profile," Thrombosis and Haemostasis, vol. 95, No. 5, May 2006, pp. 822-828.

Chandler, et al., "Development of a rapid emergency hemorrhage panel," Tranfusion, vol. 50, No. 12, Dec. 2010, pp. 2547-2552.

Chandler, et al., "Estimating the rate of thrombin and fibrin generation in vivo during cardiopulmonary bypass," Blood, vol. 101, No. 11, Jun. 2003, pp. 4355-4362.

Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.

Cohn et al., "An elasticity microscope. Part I: Methods," IEEE Transactions on Ultrasonics Ferroelectrics & Frequency Control, vol. 44, 1997, pp. 1304-1319.

Cohn et al., "An elasticity microscope. Part II: Experimental Results," IEEE Transactions on Ultrasonics Ferroelectrics & Frequency Control, vol. 44, 1997, pp. 1320-1331.

(56) References Cited

OTHER PUBLICATIONS

Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.

Dahlback, B., "Blood Coagulation," Lancet, vol. 355, No. 9215, May 2000, pp. 1627-1632.

Emelianov et al., "Ultrasound Elasticity Imaging of Deep Venous Thrombosis," Proc. IEEE Ultrasonics Symp., 2000, pp. 1791-1794.

Evans, et al., "Rheometry and associated techniques for blood coagulation studies," Medical Engineering and Physics, vol. 30, No. 6, Jul. 2008, pp. 671-679.

Fatemi et al., "C-Scan Imaging by Radiation Force Stimulated Acoustic Emission Method," Proc. IEEE Ultrasonics Symp., 1996, pp. 1459-1462.

Fatemi, et al., "Application of radiation force in noncontact measurement of the elastic parameters," Ultrasonic Imaging, vol. 21, No. 2, Apr. 1999 pp. 147-154.

Fatemi, et al., "Ultrasound-Stimulated Vibro-Acoustic Spectography," Science Magazine, vol. 280, No. 5360, 1998, pp. 82-85.

Fertner, et al., "Comparison of Various Time Delay Estimation Methods by Comptuer Simulation," IEEE Transactions on Acoustics, Speech, and Signal Processing, vol. 34, No. 5, 1986, pp. 1329-1330.

Flax, et al., "Phase-Aberration Correction Using Signals From Point Reflectors and Diffuse Scatterers: Basic Principles," IEEE Transactions on Ultrasonics Ferroelectrics & Frequency Control, vol. 35, No. 6, Nov. 1988, pp. 758-767.

Gallippi, et al., "Adaptive clutter filtering via blind source," Ultrasonic Imaging, vol. 24, No. 4, 2002, pp. 193-214.

Gallippi, et al., "BSS-based filtering of physiological and ARFI-induced tissue and blood motion," Ultrasound in Medicine and Biology, vol. 29, No. 11, 2003, pp. 1583-1592.

Gallippi, et al., "Complex blind source separation for acoustic radiation force impulse imaging in the peripheral vasculature, in vivo," IEEE Ultrasonics Symposium, vol. 1, 2004, pp. 596-601.

Gauss, et al., "Wavefront Estimation in the Human Breast," presented at SPIE Medical Imaging, vol. 4325, 2001, pp. 172-180.

Giunta, et al., "Estimation of Global Motion Parameters by Complex Linear Regression," IEEE Transactions on Image Processing, vol. 8, No. 11, 1999, pp. 1652-1657.

Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.

Hartley, et al., "Doppler Measurement of Acoustic Streaming," IEEE Ultrasonics Symposium Proceedings, 1995, pp. 1537-1540.

Huang, et al., "Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.

Huang, et al., "Detection of blood coagulation and clot formation using quantitative ultrasonic parameters," Ultrasound in Medicine and Biology, vol. 31, No. 11, Nov. 2005, pp. 1567-1573.

Jacovitti, et al., "Discrete Time Techniques for Time Delay Estimation," IEEE Transactions on Signal Processing, vol. 41, No. 2, Feb. 1993, pp. 525-533.

Jensen, "A New Method for Estimation of Velocity Vectors," IEEE Transactions on Ultrasonics, Ferroelectrics and Frequency Control, vol. 45, No. 3, 1998, pp. 837-851.

Jensen, Estimation of Blood Velocities Using Ultrasound, 1996, pp. 195-225.

Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.

Jolliffe, It., "Principal Component Analysis," Springer Series in Statistics, 2nd edition, Springer, NY, 2002, pp. 1-8.

Kadi, et al., "On the performance of regression and step-initialized IIR Clutter Filters," IEEE Transactions on Ultrasonics, Ferroelectrics, and Frequency Control, vol. 42, 1995, pp. 827-837.

Kasai, et al., "Real-time Two-Dimensional Blood Flow Imaging Using an Autocorrelation Technique," IEEE Ultrasonics Symposium, vol. 32, No. 3, 1985, pp. 458-464.

Kruse, et al., "A new high resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.

Ledoux, et al., "Reduction of the clutter component in Doppler ultrasound signals based on singular value decomposition: a simulation study," vol. 19, No. 1, 1997, pp. 1-18.

Lerner, et al., "Sono-elasticity: medical elasticity images derived from ultrasound signals in mechanically vibrated targets," Ultrasound in Medicine & Biology, vol. 16, 1998, pp. 317-327.

Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.

McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.

Nielson, er al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.

Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.

O'Donnell, et al., "Internal Displacement and Strain Imaging using Ultrasonic Speckle.Tracking," IEEE Transactions on Ultrasonics, Ferroelectrics and Frequency Control, vol. 41, 1994, pp. 314-325.

Ophir, et al., "Elastography: A Quantitative Method for Imaging the Elasticity of Biological Tissues," Ultrasonic Imaging, vol. 13, No. 2, 1991, pp. 111-134.

Patil, et al., "3D prostate elastography: algorithm, simulations and experiments," Physics in Medicine & Biology, vol. 52, No. 12, 2007, pp. 3643-3663.

Perry, et al., "Point-of-care testing in haemostasis," British Journal of Haematology, vol. 150, No. 5, Sep. 2010, pp. 501-514.

Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.

Keresztes, et al., "The PFA-100: analysis and interpretation of a platelet function measurement," The Journal of Cardiovascular Nursing, vol. 20, No. 6, 2005, pp. 405-407.

Kettner, S.C., et al., "Use of abciximab-Modified Thrombelatography in Patients Undergoing Cardiac Surgery," Anesth Analg, vol. 89, 1999, pp. 580-584.

Khurana, Sandeep, et al., "Monitoring Platelet Glycoprotein IIb/IIa-fibrin Interaction with Tissue Factor-Activated Thromboelastography," J Lab Clin Med, vol. 130, No. 4, 1997, pp. 401-411.

Khurana, Sandeep, et al., "Thromboelastography Can Rapidly Bioassay Fibrinogen," Anesthesiology, vol. 85, No. 3A, Sep. 1996, p. A457.

Koepke, J., "Point-of-Care Coagulation Testing," Laboratory Medicine, vol. 31, No. 6, Jun. 2000, pp. 343-346.

Lubinski, et al., "Adaptive strain estimation using retrospective processing medical US elasticity imaging," IEEE Transactions on Ultrasonics Ferroelectrics & Frequency Control, vol. 46, 1999, pp. 97-107.

Mahla, et al., "Thromboelastography for monitoring prolonged hypercoagulability after major abdominal surgery," Anesthesia and Analgesia, vol. 92, No. 3, Mar. 2001, pp. 572-577.

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

(56) References Cited

OTHER PUBLICATIONS

Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.
Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.
Nightingale, et al., "Acoustic Radiation Force Impulse Imaging: In Vivo Demonstration of Clinical Feasibility," Ultrasound in Medicine & Biology, vol. 28, 2002, pp. 227-235.
Nightingale, et al., "Acoustic remote palpation: initial in vivo results," presented at IEEE Ultrasonics Symposium, 2000, pp. 1553-1558.
Oberhardt, et al., "Dry reagent technology for rapid, convenient measurements of blood coagulation and fibrinolysis," Clinical Chemistry, vol. 37, No. 4, Apr. 1991, pp. 520-526.
O'Donnell, et al., "Role of the Thrombelastograph as an adjunctive test in thrombophilia screening," Blood Coagulation and Fibrinolysis, vol. 15, No. 3, Apr. 2004, pp. 207-211.
Packham, M., "Role of platelets in thrombosis and hemostasis," Canadian Journal of Physiology and Pharmacology, vol. 72, No. 3, Mar. 1994, pp. 278-284.
Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.
Parsons, et al., "Age Determiniation of Experimental Venous Thrombi by Ultrasonic Tissue Characterization," Journal of Vascular Surgery, vol. 17, 1993, 470-478.
Pivalizza, et al., "Perioperative thromboelastography and sonoclot analysis in morbidly obese patients," Canadian Journal of Anaesthesia, vol. 44, No. 9, Sep. 1997, pp. 942-945.
Rao, G., "Need for a point-of-care assay for monitoring antiplatelet and antithrombotic therapies," Stroke, vol. 40, No. 6, Jun. 2009, pp. 2271-2272.
Riou, et al., "Fast adaptive eigenvalue decomposition: a maximum likelihood approach," IEEE International Conference on Acoustics, Speech, and Signal Processing, vol. 5, 1997, pp. 3565-3568.
Rubin, et al., "Clinical application of sonographic elasticity imaging for aging of deep venous thrombosis: preliminary findings," Journal of Ultrasound in Medicine, vol. 22, 2003, pp. 443-448.
Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.
Srinivasan, et al., "Elastographic imaging using staggered strain estimates," Ultrasonic Imaging, vol. 24, 2002, pp. 229-245.
Strobach, P., "Low-rank adaptive filters," IEEE Trans Signal Process, vol. 44, No. 12, 1996, pp. 2932-2947.
Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993;71:9-15.
Vig, et al., "Thromboelastography: a reliable test?," Blood Coagulation and Fibrinolysis, vol. 12, No. 7, Oct. 2001, 555-561.
Viola, et al., "A Comparison between spline-based and phase-domain time-delay estimators," IEEE Transactions on Ultrasonics, Ferroelectrics, and Frequency Control, vol. 53, No. 3, 2006, pp. 515-517.
Viola, et al., "A comparison of the performance of time-delay estimators in medical ultrasound," IEEE Transactions on Ultrasonics Ferroelectrics & Frequency Control., vol. 50, 2003, pp. 392-401.
Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker, et al., "A Fundamental Limit on the Accuracy of Speckle Signal Alignment," IEEE Ultrasonics Symposium Proceedings, vol. 3, 1994, pp. 1787-1791.
Walker, et al., "A Method of Imagining Viscoelastic Parameters with Acoustic Radiation Force," Physics in Medicine and Biology, vol. 45, No. 6, 2000, pp. 1437-1447.
Whitten, et al., "Thromboelastography: past, present, and future," Anesthesiology, vol. 92, No. 5, May 2000, pp. 1223-1225.
Gaetano, G. de, et al., "Effect of Platelets on Clot Structuration, a Thrombelastographic Study", Thrombosis Research, vol. 3 No. 4, pp. 425-435, 1973.
Glidden, Paul F., et al., "Thromboelastograph Assay for Measuring the Mechanical Strength of Fibrin Sealant Clots", Clinical and Applied Thrombosis/Hemostasis, vol. 6 No. 4 , 226-233, Oct. 2000.
Grelich, Philip E., et al., "A Modified Thromboelastographic Method for Monitoring c7E3 Fab in Heparinized Patients", Anesth Analg, vol. 84, pp. 31-38, 1997.
Grelich, Philip E., et al., "Near-Site Monitoring of the Antiplatelet Drug Abciximad Using the Hemodyne Analyzer and Modified Thrombelastograph", Journal of Cardiothoracic and Vascular Anethesia, vol. 13 No. 1, pp. 58-64, Feb. 1999.
Gottumukkala, Vijaya N., et al., "Assessing Platelet and Fibrinogen Contribution to Clot Strength Using Modified Thromboelastography in Pregnant Women", Anesth Analg, vol. 89, pp. 1453-1455, 1999.
Kettner, S.C., et al., "Use of abciximab-Modified Thrombelatography in Patients Undergoing Cardiac Surgery", Anesth Analg, vol. 89, pp. 580-584, 1999.
Khurana, Sandeep, et al., "Monitoring Platelet Glycoprotein IIb/IIa-fibrin Interaction with Tissue Factor-Activated Thromboelastography", J Lab Clin Med, vol. 130, No. 4, pp. 401-411, 1997.
Khurana, Sandeep, "Thromboelastography Can Rapidly Bioassay Fibrinogen", Anesthesiology, vol. 85, No. 3A, pp. A457, Sep. 1996.
Anderson, "Preventing Deep Vein Thrombosis and Pulmonary Embolism" Center for Outcomes Research, U Mass Med Center 1998, 23 pgs.
Beer: Center for Reproductive Immunology & Genetics, "Thrombophilia: Inherited and Acquired," 6 pgs. http://repro-med.net/papers/thromb.php.
Bilgen, et al. "Error analysis in acoustic elastography. II. Strain estimation and SNR analysis," Journal of the Acoustical Society of America, vol. 101, 1997, pp. 1147-1154.
Bercoff et al. "In vivo bteast tumor detection using transient elastography," Ultrasound in Medicine & Biology, vol. 29, 2003, pp, 1387-1396.
Chaturvedi, et al. "Testing the limitations of 2-D companding for strain imaging using phantoms," IEEE Transactions on Ultrasonics Fetroelectrics & Frequency Control, vol. 45, 1998, pp. 1022-1031.
Cohn et al. "An elasticity microscope. Part I: Methods," IEEE Transactions on Ultrasonics Ferroelectrics & Frequency Control, vol. 44, 1997, pp. 1304-1319.
Cohn et al. "An elasticity microscope. Part II: Experimental Results" vol. 44, 1997, pp. 1320-1331.
Emelianov et al. "Ultrasound Elasticity Imaging of Deep Venous Thrombosis," 2000, pp. 1791-1794.
Freedman, et al. "A Meta-Analysis of Thromboembolic Prophylaxis Following Elective Total Hip Arthroplasty" Journal of Bone and Joint Surgery, vol. 82-A, 2000, pp. 929-938.
Fatemi et al. "Ultasound-Stimulated Vibro-Acoustic Spectrography," vol. 280, 1998, pp. 82-85.
Fatemi et al. "C-Scan Imaging by Radiation Force Stimulated Acoustic Emission Method," Proc. IEEE Ultrasonics Symp., 1996, pp. 1459-1462.
Fertner et al. "Comparison of Various Time Delay Estimation Methods by Computer Simulatoin," vol. 34, 1986, 1329-1330.
Gauss et al. "Adaptive Imaging in the Thyroid Using Fundamental and Harmonic Echo Data," presented at IEEE Ultrasonics Symposium, 1999, pp. 1515-1519.
Gauss et al. "Wavefront Estimation in the Human Breast," presented at SPIE Medical Imaging, vol. 4325, 2001, pp. 172-180.
Harris et al. "Evaluation of recurrent thrombosis and hypercoagulability" American Family Physician, vol. 56, 1997, 6 pgs.

(56) References Cited

OTHER PUBLICATIONS

Hirsh et al, "Management of deep vein thrombosis and pulmonary embolism. A statement for healthcare professionals. Council on Thrombosis (in consultation with the Council on Cardiovascular Radiology), American Heart Association" vol. 93, 1996, 55 pgs.
Hirsh et al. "How we diagnose and treat deep vein thrombosis," Blood, vol. 99, 2002, pp. 3102-3110.
Hartley et al.; Characteristics of Acoustic Streaming Created and Measured by Pulsed Doppler Ultrasound pp. 1278-1285, vol. 44 No. 6, Nov. 1997.
Hartley. Doppler Measurement of Acoustic Streaming. pp. 1537-1540 1995.
Jensen et al. "Calculation of pressure fields from arbitrarily shaped, apodized, and excited ultrasound transducers," IEEE Transactions on Ultrasonics, Ferroelectrics, and Frequency Control, vol. 39, pp. 192, 262-267.
Lerner et al. "Sono-elasticity: medical elasticity images derived from ultrasound signals in mechanically vibrated targets," vol. 16, 1988, pp. 317-327.
Lubinski et al. "Adaptive strain estimation using retrospective processing medical US elasticity imaging," IEEE Transactions on Ultrasonics Ferroelectrics & Frequency Control, vol. 46, 1999, pp. 97-107.
McAleavey et al. "Estimates of echo correlation and measurement bias in acoustic radiation force impulse imaging," IEEE Transactions on Ultrasonics Ferroelectrics & Frequency Control, vol. 50, 2003, pp. 631-641.
Nightingale et al. "Acoustic remote palpation: initial in vivo results," presented at IEEE Ultrasonics Symposium; 2000; pp. 1553-1558.
Nightingale et al. "Acoustic Radiation Force Impulse Imaging. In Vivo Demonstration of Clinical Feasibility," Ultrasound in Medicine & Biology, vol. 28, 2002, pp. 227-235.
Nightingale at al. Shear-Wave Generation Using Acoustic Radiation Force: In Vivo and EX Vivo Results, vol. 29, No. 12, 2003, pp. 1715-1723.
O'Donnell et al. "Internal Displacement and Strain Imaging using Ultrasonic Speckle Tracking," IEEE Transactions on Ultrasonics. Ferroelectrics and Frequency Control, vol. 41, 1994, pp. 314-325.
Ophir et al. "Elastography: A Quantitative Method for Imaging the Elasticity of Biological Tissues," vol. 13, 1991, pp. 111-134.
Parsons, et al, "Age Determination of Experimental Venous Thrombi by Ultrasonic Tissue Characterization," Journal of Vascular Surgery, vol. 17, 1993, 470-478.
Rubin et al., "Clinical application of sonographic elasticity imaging for aging of deep venous thrombosis. preliminary findings," Journal of Ultrasound in Medicine, vol. 22, 2003, pp. 443-448.
Sugimoto et al. "Tissue Hardness Measurement Using the Radiation Force of Focused Ultrasound," Proc. IEEE Ultrason. Symp., 1990, pp. 1377-1380.
Shung et al "Ultrasonic characterization of blood during coagulation," Journal of Clinical Ultrasound, vol. 12, 1984, pp. 147-153.
Sarvazyan et al. "Shear Wave Elasticity Imaging—A New Ultrasonic Technology of Medical Diagnostics," Ultrasound in Medicine and Biology, vol. 24, 1998, pp. 1419-1436.
Sakharov et al., Acceleration of Fibrinolysis by High-Frequency Ultrasound. The Contribution of Acoustic Streaming and Temperature Rise. pp. 333-340, 2000.
Shi et al., Experimental Investigation and Finite Element Simulation of Streaming in Blood in Cylindrical Models. pp. 1509-1512, 2000.
Shi et al., Color Doppler imaging of acoustic streaming in blood and clot. pp. 1315-1318, 1999.
Shi et al., Color Doppler Detection of Acoustic Streaming in a Hematoma Model. pp. 1255-1264, vol. 27, No. 9, 2001.
Shi, Quantitative Investigation of Acoustic Streaming in Blood, pp. 1110-1121, J. Acoust. Soc. Am. 111, Feb. 2002, pp. 110-1121.
Torr, "The Acoustic Radiation Force," Am. J. Phys., vol. 52, 1984,pp. 402-408.
Viola et al "A comparison of the performance of time-delay estimators in medical ultrasound," IEEE Transactions on Ultrasonics Ferroelectrics & Frequency Control, vol. 50, 2003, ,pp. 382-401.

Viola et al. "Sonorheometry: A Noncontact Method for the Dynamic Assessment of Thrombosis," The Annals of Biomedical Engineering, vol. 32, 2004, pp. 696-705.
Viola et al, "Ultrasound echo decorrelation due to acoustic radiation force," vol. 2, 2002, pp. 1903-1906.
Viola et al. "Radiation Force Imaging of Viscoelastic Properties with Reduce Artifacts." vol. 50, 2003, pp. 736-742.
Viola et al. "Comparison of Time Delay Estimators in Medical Ultrasound," 2001, pp. 1485-1488.
Viola et al "A Spline Based Algorithm for Continuous Time Delay Estimation Using Sampled Data," IEEE Transactions on Ultrasonics Ferroelectrics & Frequency Control, in press. 56 pgs. Download Mar. 7, 2005.
Viola et al. "Imaging Viscoelastic Properties of the Vitreous" 2001, pp. 1623-1626.
Viola et al. "Efficient and Accurate Spline-Based Time Delay Estimation" 4 pgs. Download Mar. 16, 2005.
Viola et al., Analysis of Clot Formation with Acoustic Radiation Force. pp. 235-242 & pp. 1-2, vol. 4689, 2002.
Walker, et al. "A Fundamental Limit on the Accuracy of Speckle Signal Alignment," 1994, pp. 1787-1791.
Walker et al. "A Method of Imaging Viscoelastic Parameters with Acoustic Radiation Force," vol. 45, 2000, pp. 1437-1447.
Walker et al "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker et al. "Real-Time Imaging of Tissue Vibration Using a Two-Dimensional Speckle Tracking System," IEEE Ultrason. Symp , 1993, pp. 873-877.
Walker et al "Applications of Acoustic Radiation Force in Ophthalmic Ultrasound," Proc. IEEE Ultrason. Symp., vol. 2, 1997, pp. 1291-1295.
Walker et al. "The Significance of Correlation in Ultrasound Signal Processing," 2001, 13 pgs.
Webster, Medical Instrumentation: Application and Design, New York: John Wiey & Sons, 1998, 6 pgs.
US 6,135,954, 10/2000, Cohen et al. (withdrawn).
Beer: Center for Reproductive Immunology & Genetics, "Thrombophilia: Inherited and Acquired," 6 pages, http://repro-med.net/papers/thromb.php.
Bell, et al., "Thrombelastographic evaluation of coagulation in transurethral prostatectomy," British Journal of Urology, vol. 78, No. 5, 1996, pp. 737-741.
Bombeli, et al., "Updates in perioperative coagulation: physiology and management of thromboembolism and haemorrhage," British Journal of Anaesthesia; vol. 93, No. 2, Aug. 2004, pp. 275-287.
Chavez, J., "A novel thrombelastograph tissue factor/kaolin assay of activated clotting times for monitoring heparin anticoagulation during cardiopulmonary bypass," Anesthesia and Analgesia; vol. 99, No. 5 Nov. 2004, pp. 1290-1294.
Curry, et al., "Convention and near-patient tests of coagulation," British Journal of Anaesthesia, vol. 7, No. 2, Apr. 2007, pp. 45-50.
Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.
Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.
Ferraris, et al., "2011 Update to the Society of Thoracic Surgeons and the Society of Cardiovascular Anesthesiologists Blood Conservation Clinical Practice Guidelines," Annals of Thoracic Surgery, vol. 91, 2011, pp. 944-982.
Freedman, et al., "A Meta-Analysis of Thromboembolic Prophylaxis Following Elective Total Hip Arthroplasty," Journal of Bone and Joint Surgery, vol. 82-A, 2000, pp. 929-938.
Gaetano, G. de, et al., "Effect of Platelets on Clot Structuration, a Thrombelastographic Study," Thrombosis Research, vol. 3, No. 4, pp. 425-435, 1973.

(56) References Cited

OTHER PUBLICATIONS

Ganter, et al., "Active, personalized, and balanced coagulation management saves lives in patients with massive bleeding," Anesthesiology, vol. 133, No. 5, Nov. 2010, pp. 1016-1018.
Ganter, et al., "Coagulation monitoring: current techniques and clinical use of viscoelastic point-of-care coagulation devices," Anesthesia and Analgesia, vol. 106, No. 5, May 2008, pp. 1366-1375.
Gauss, et al., "Adaptive Imagining in the Thyroid Using Fundamental and Harmonic Echo Data," presented at IEEE Ultrasonics Symposium, 1999, pp. 1515-1519.
Glidden, Paul F., et al., "Thromboelastograph Assay for Measuring the Mechanical Strength of Fibrin Sealant Clots," Clinical and Applied Thombosis/Hemostasis, vol. 6, No. 4, Oct. 2000, pp. 226-233.
Gottumukkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.
Greilich, Philip E., et al., "A Modified Thromboelastographic Method for Monitoring c7E3 Fab in Heparinized Patients," Anesth Analg, vol. 84, 1997, pp. 31-38.
Greilich, Philip E., et al., "Near-Site Monitoring of the Antiplatelet Drug Abciximad Using the Hemodyne Analyzer and Modified Thrombelastograph," Journal of Cardiothoracic and Vascular Anesthesis, vol. 13, No. 1, Feb. 1999, pp. 58-64.
Gurbel, et al., "Platelet function monitoring in patients with coronary artery disease," Journal of the American College of Cardiology, vol. 50, No. 19, Nov. 2007, pp. 1822-1834.
Harris, et al., "Evaluation of recurrent thrombosis and hypercoagulability," American Family Physician, vol. 56, No. 6, Oct. 1997, pp. 1591-1596, pp. 1601-1602.
Hett, et al., "Sonoclot Analysis," British Journal of Anaesthesia, vol. 75, No. 6, Dec. 1995, pp. 771-776.
Hirsh, et al., "How we diagnose and treat deep vein thrombosis," Blood, vol. 99, 2002, pp. 3102-3110.
Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.
Hoffman, et al., "A cell-based model of hemostasis," Thrombosis and Haemostasis, vol. 85, No. 6, Jun. 2001, pp. 958-965.
Ickx, Brigitte, "Point-of-Care Monitoring of Haemostasis in the OR and the ICU," European Society of Anaesthesiologists. Jun. 5, 2004, pp. 79-83.
International Search Report and Written Opinion of the International Searching Authority, received in corresponding application PCT/US2010/049342, Nov. 16, 2010.
International Search Report and Written Opinion of the International Searching Authority, received in corresponding application PCT/US2011/031832, Dec. 15, 2011.
Ivandic, et al., "Determination of clopidogrel resistance by whole blood platelet aggregometry and inhibitors of the P2Y12 receptor," Clinical Chemistry, vol. 52, No. 3, Mar. 2006, pp. 383-388.
Sarvazyan, et al., "Shear Wave Elasticity Imagining—A New Ultrasonic Technology of Medical Diagnostics," Ultrasound in Medicine and Biology, vol. 24, 1998, pp. 1419-1436.
Shi, Quantitative Investigation of Acoustic Streaming in Blood, J. Acoust. Soc. Am. 111, Feb. 2002, pp. 1110-1121.
Shi, et al., "Color Doppler Detection of Acoustic Streaming in a Hematoma Model," Ultrasound in Medicine and Biology, vol. 27, No. 9, 2001, pp. 1255-1264.
Shi, et al., "Color Doppler imaging of acoustic streaming in blood and clot," IEEE Ultrasonics Symposium, vol. 2, 1999, pp. 1315-1318.
Shi, et al., "Experimental Investigation and Finite Element Simulation of Streaming in Blood in Cylindrical Models," IEEE Ultrasonics Symposium, vol. 2, 2000, pp. 1509-1512.
Shung, et al., "Ultrasonic characterization of blood during coagulation," Journal of Clinical Ultrasound, vol. 12, No. 3, 1984, pp. 147-153.
Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.
Sugimoto, et al., "Tissue Hardness Measurement Using the Radiation Force of Focused Ultrasound," Proc. IEEE Ultrason. Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Viola, et al., "A Spline Based Algorithm for Continuous Time Delay Estimation Using Sampled Data," IEEE Transactions on Ultrasonics Feffoelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Sonorheometry: A new Method for Assessing coagulation potential," IEEE Ultrasonics Symposium, vol. 1, 2007, pp. 1001-1004.
Viola, et al., "Sonorheometry: A Noncontact Method for the Dynamic Assessment of Thrombosis," The Annals of Biomedical Engineering, vol. 32, 2004, pp. 696-705.
Viola, et al., "Ultrasound echo decorrelation due to acoustic radiation force," IEEE Ultrasonics Symposium Proceedings, vol. 2, 2002, pp. 1903-1906.
Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Yu, et al., "Single-Ensemble-Based Eigen-Processing Methods for Color Flow Imaging," IEEE Transactions on Ultrasonics, Ferroelectrics, and Frequency Controls, vol. 55, No. 3, 2008, pp. 573-587.

METHOD AND APPARATUS FOR CHARACTERIZATION OF CLOT FORMATION

CROSS-REFERENCE

This application is a division of application Ser. No. 10/971,178, filed Oct. 22, 2004, which is incorporated herein by reference in its entirety and to which application we claim priority under 35 USC §120; and which application claims the benefit of U.S. Provisional Application No. 60/513,264, filed Oct. 22, 2003, which application is incorporated herein, in its entirety, by reference thereto.

GOVERNMENT RIGHTS

This invention was made with government support under federal grant no. GAAN P200A010433 awarded by the Department of Education. The United States Government may have certain rights in this invention.

BACKGROUND OF THE INVENTION

Blood coagulation is a delicately regulated process that serves as a protective mechanism against blood loss due to tissue damage. Overactive or unregulated coagulation can lead to conditions including myocardial infarction, stroke, deep vein thrombosis (DVT), and pulmonary embolism. The ability to recognize coagulation disorders and quantify their severity is critical for identifying those at risk and implementing appropriate prophylactic treatment. Because of inherent risks accompanying anticoagulant therapy, such as hemorrhage or anaphylaxis, it is critical that such therapies be prescribed appropriately (see Anderson et al., "Best Practices: Preventing Deep Vein Thrombosis and Pulmonary Embolism", Center for Outcomes Research, U. Mass. Med. Ctr, 1998, which is hereby incorporated herein, in its entirety, by reference thereto).

Hypercoagulability, or thrombophilia, is an inherited or acquired coagulation disorder in which there is either an overactivation of coagulation or deficient deactivation of developed thrombus. While a number of factors within the coagulation cascade such as factor V Leiden, protein C or S deficiency, and antithrombin III deficiency are known to increase the propensity to clot (see Harris et al. "Evaluation of Recurrent Thrombosis and Hypercoagulability", American Family Physician, vol. 56 (6), Oct. 15, 1997, which is hereby incorporated herein, in its entirety, by reference thereto), there is currently a dearth of techniques available to quantify these effects clinically. The methods currently available are mostly biochemical in nature and test for a specific genetic mutation or abnormal chemical reaction rate, such as Leiden Factor V. mutation R560Q; Hyperhomocysteinemia MTHFR Mutation; Prothrombin Gene Mutation 20210; Protein C levels; Protein S levels; Activated Protein C activity; antibodies to six phospholipids of the IgM, IgG and IgA classes; Lupus anticoagulant antibody; Russell Viper Venom time; Activated Partial Thromboplastin time; and Prothrombin time; see http://repromed.net/papers/thromb.php which is incorporated herein; in its entirety, by reference thereto. While these tests may provide valuable information, they are unable to determine the coagulation rate of an individual's blood. Furthermore, since the coagulation cascade is exceedingly complex, there are numerous steps in the pathway that might be disrupted or inappropriately regulated. However, it is not always possible to determine if these interruptions in the cascade are predictive of an observable clinical impact on thrombus formation.

Mechanical methods, such as cone and plate viscometry or indentation testing, provide the most intuitive way to characterize the mechanical parameters of blood coagulation. However, these approaches are limited because the mechanical forces applied to the forming thrombus can disrupt its delicate structure, and thus disturb the system enough to interrupt the normal course of coagulation.

Deep vein thrombosis (DVT) refers to the formation of a blood clot in a large vein of the leg, DVT often results from a lack of movement in the extremities for significant periods of time or from an increased propensity to clot due to malignancy, recent surgery or trauma, pregnancy, hormonal agents such as oral contraceptives, or other contributing causes, see Hirsh et al., "How We Diagnose and Treat Deep Vein Thrombosis", Blood, vol. 99(1), pp. 3102-3110, which is hereby incorporated herein, in its entirety, by reference thereto. If a portion of the thrombus breaks off and travels to the pulmonary vessels, a potentially fatal pulmonary embolism can result. Clinical diagnosis cannot serve as the sole means of DVT diagnosis because many potentially dangerous venous thrombi are asymptomatic, and many of the symptoms are not unique to DVT. Current noninvasive methods of diagnosis such as duplex ultrasonography, venography, impedance plethysmography, and MRI can often detect the presence of a clot, but are limited by an inability to determine the stage of development of the clot so identified. Furthermore, these methods must often be used in conjunction with another diagnostic method or tool such as the d-dimer assay in order to make a conclusive diagnosis.

Although duplex ultrasonography is favored for the initial investigation of DVT, several groups have also proposed the use of ultrasound to extrapolate parameters related to the formation of DVT. Shung et al, in "Ultrasonic Characterization of Blood During Coagulation", Journal of Clinical Ultrasound, vol. 12, pp 147-153, 1984 (which is hereby incorporated herein, in its entirety, by reference thereto), have shown that the increase in echogenicity associated with the formation of a thrombus is mostly due to an increase in ultrasonic backscatter. They have also found increases in both the attenuation coefficient and the speed of sound. Parsons et al. in "Age Determination of Experimental Venous Thrombi by Ultrasonic Tissue Characterization", Journal of Vascular Surgery, vol. 17(3), pp. 470-478, 1993 (which is hereby incorporated herein, in its entirety, by reference thereto), have been able to differentiate in vivo between clots of varying ages by looking a the slope and intercept of the linear fit of the normalized power spectrum. Emelianov et al., in "Ultrasound Elasticity Imaging of Deep Vein Thrombosis" Proc. IEEE Ultrasonic Symposium, 2000 (which is hereby incorporated herein, in its entirety, by reference thereto), have characterized different clinical stages of a thrombus using maps of local strain. Their method operates by obtaining baseline radio frequency (RF) echo data, mechanically compressing the tissue, obtaining a second compressed set of data, and applying signal processing methods to create maps of local strain. Rubin et al., in "Clinical application of sonographic elasticity imaging for aging of deep venous thrombosis: preliminary findings," Journal of Ultrasound in Medicine, vol. 22, pp. 443-8, 2003, which is incorporated herein, in its entirety, by reference thereto, characterizes different clinical stage of a thrombus using maps of local strain obtained by compressive elastography. Although the techniques proposed by Parsons et al., Emelianov et al. and Rubin et al. have yielded valuable results, they are primarily focused on age classification of DVT and thus are not able to characterize thrombus formation. Furthermore, these techniques do not provide information about coagulability and are thus of little or no value in prospectively identifying patients at high risk of forming a blood clot. Furthermore, direct translation of these techniques to benchtop tools is problematic because of high variability in measurements taken.

There remains a need for the ability to characterize changes in soft tissue, and particularly for characterizing thrombus formation. There remain needs for methods, apparatus and systems that can characterize thrombus formation for diagnosis and treatment purposes, and preferably in a substantially non-invasive manner.

SUMMARY OF THE INVENTION

The present invention provides methods of characterizing at least one physical property of soft tissue. One such method described herein includes generating a series of acoustic pulses and directing them into the soft tissue to be characterized, wherein at least one of the pulses is of sufficiently high intensity to induce physical displacement of the tissue. At least one physical property of the tissue is estimated based on measurement of at least two of the pulses as reflected from the soft tissue and/or receiving optical reflections from the soft tissue as the soft tissue is being physically displaced. The process may be repeated at least once after passage of a time interval, so that time-based data can be generated.

An apparatus for identifying changes in at least one physical parameter of a soft tissue over time includes an acoustic wave generator capable of repeatedly generating acoustic pulses of sufficient intensity to induce measurable physical displacement in the soft tissue; a sensor adapted to sense at least one of optical waves or the acoustic pulses after reflection by the soft tissue; a clock governing cycles during which the acoustic pulses are generated and during which sensing of at least one of the acoustic or optical waves is carried out; and a processor that receives input from the sensor and clock and calculates time-based data characterizing at least one characteristic of the physical displacement induced.

A method of characterizing at least one physical property of blood is described, including generating a series of acoustic pulses and directing the series of pulses into the blood such that at least one of the pulses is of sufficiently high intensity to induce physical displacement of the blood; measuring a displacement of the blood resulting from the induced physical displacement thereof; and estimating at least one characteristic of the physical displacement based on the measurement.

Methods of diagnosis of the development stages of clotting are described.

Methods of evaluating effectiveness of anti-clotting treatments are described.

Methods of evaluating effectiveness of pro-clotting treatments are also described.

These and other advantages and features of the invention will become apparent to those persons skilled in the art upon reading the details of the methods, apparatus and systems as more fully described below.

DETAILED DESCRIPTION OF THE INVENTION

Figure 1A:
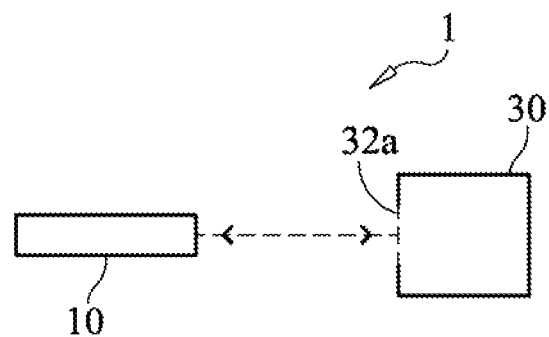
FIG. 1A is a schematic representation of the present invention useful for in vitro characterization of a soft tissue sample.

Before the present methods, apparatus and systems are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a transducer" includes a plurality of such transducers and reference to "the curve" includes reference to one or more curves and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention provides methods, apparatus and systems for performing what the present inventors have termed sonorheometry. Sonorheometry provides data about the mechanical properties of soft tissue. Furthermore, repeated measurements using sonorheometry enable characterization of changing properties over time. Sonorheometry is particularly well-suited to characterizing blood coagulation. The present invention provides data about the mechanical properties of a developing thrombus without disrupting its formation. The methods and techniques may be non-invasive or carried out in a laboratory setting after obtaining a sample from a patient, and are based on the application of acoustic radiation force to the tissue to be characterized.

An increased or decreased propensity to clot can be evaluated by observing the coagulation rate and mechanical characteristics of the developing thrombus at any time during formation. This information may in turn allow clinicians to assess an individual's clotting behavior and to treat coagulation disorders appropriately. This information may also be used to evaluate whether a particular treatment and/or dosage is effective or needs to be changed, as subsequent testing according to the present methods (i.e., after a treatment has been administered) can be carried out to compare the results, thereby indicating the effect of the treatment.

Referring now to FIG. 1, an assembly 1 is schematically shown that is set up for testing soft tissue according to the present invention. An acoustic wave generating device 10 is positioned in alignment with container 30 to allow device 10 to irradiate a soft tissue contained within container 30. Device 10 may be mounted or fixed at a predetermined distance for the contents of the container 30 to receive focused acoustical waves from device 10. Thus, device 10 and container 30 are oriented to align the emission of acoustic waves from device 10 with a sample contained in container 30. Container 30 may be entirely acoustically transparent, or contains at least one window 32a that is acoustically transparent and that is aligned with the emission pathway of device 10. As one non-limiting example; container 30 may include a plastic cuvette having windows 32a32d cut therethrough and covered with KAPTON® (polyimide) film or other acoustically transparent film. One knowledgeable in the art will realize that it may be advantageous to place the acoustic window or windows of the sample container at some non-perpendicular angle relative to the direction of wave propagation so as to reduce the magnitude of received echoes from the interfaces with the window(s). Multiple measurements may be performed at the same time using an array of sample containers 30, for example. One knowledgeable in the art will recognize that such an array may either consist of individual containers, or a single container with multiple sample compartments. Additionally or alternatively, an array of transducers may be included in device 10, or an array of devices 10 may be used to make multiple measurements. Thus, for example, multiple transducers and/or multiple devices 10 may be provided to analyze multiple samples in parallel, wherein the multiple samples are contained in multiple individual containers or a single container with multiple sample compartments.

Assembly 1 may be submerged in a tank of water or other coupling medium to facilitate transmission of the acoustic waves. Alternatively, device 10 (or other acoustic emitter and receiver) may be placed in direct contact with the sample. Still further, device 10 may be adapted to deposit the sample directly in contact therewith, for example placing a drop (or other quantity) of blood on a transducer contained in device 10 or other application feature of device 10. In the case where a bath (of water or other coupling medium) is provided, the bath may be a constant temperature bath or other means may be provided to maintain a constant sample temperature. In cases where no bath is used, it may be advantageous to place the sample in contact with a material of controlled temperature, so as to control the sample temperature. Another alternative is the use of device 10 invasively. For example, device 10 may be inserted intravascularly and delivered to the location of a stent to characterize any clotting that may be occurring as well as characterize the progression or stage of a clot that may be present. Similar intravascular techniques can be applied for identifying and/or characterizing clot processes with regard to DVT, as well as for other clotting events throughout the body, as long as the location is accessible by catheter or other delivery instrument, for example. Thus, not only are intravascular insertions, deliveries or locations mad possible by the device, but the device may also be positioned at an intracavity location or other location inside of the body.

Device 10 includes an acoustic wave generating source capable of generating one or more pulses, at least one of which is of sufficient intensity to induce measurable physical displacement in the soft tissue contained in container 30. For example, device 10 may include one or more piezoelectric transducers capable of generating ultrasonic waves. Alternatively, device 10 may utilize an electric circuit to generate rapid heating and thereby generate acoustic energy. Further alternatives may be employed for generating acoustic energy, including, but not limited to: an ultrasonic generator fabricated using microelectromechanical systems (MEMS); a capacitive micromachined ultrasound transducer; a laser used to heat a target material thereby generating acoustic energy, where the laser may be targeted on a permanent component of the assembly, or on a surface of the sample, for example. Still further alternatively, a transducer may be incorporated into the sample container 30 in lieu of providing it in the device 10, as in a case, for example, where a polymer transducer material such as PVDF may be glued right onto the surface of the sample container 30.

Device 10 further includes at least one sensor capable of measuring displacement or deformation induced by the acoustic waves as they are applied to the soft tissue sample and reflected by the soft tissue sample back to device 10. In this configuration, an ultrasound sensor may be used to track the motion of the sample as induced by at least one ultrasonic wave of sufficient intensity to induce displacement of the tissue. Alternatively, tracking of the motion may be accomplished by means other than sensing reflected acoustic waves. For example, optical coherence tomography, a focused light interferometer or laser Doppler may be used to optically sense the displacement of the tissue induced by the one or more ultrasonic waves. Device 10 may include one or more sensors for carrying out any of these optical methods or such sensors may be provided in equipment that is separate from device 10. Likewise, for acoustic sensing, the one or more sensors may be one and the same as the acoustic wave generator, or may be a separate component(s) and may take any of the forms described above with regard to the acoustic wave generating component. Typically, an ultrasonic transducer may be used to both apply ultrasonic waves to the soil tissue as well as to sense ultrasonic waves reflected back from the tissue. An adjoining processor (not shown in FIG. 1) may be provided to control the timing of transmission of pulses and of receiving of echoes (reflected pulses) by device 10.

Figure 1B:
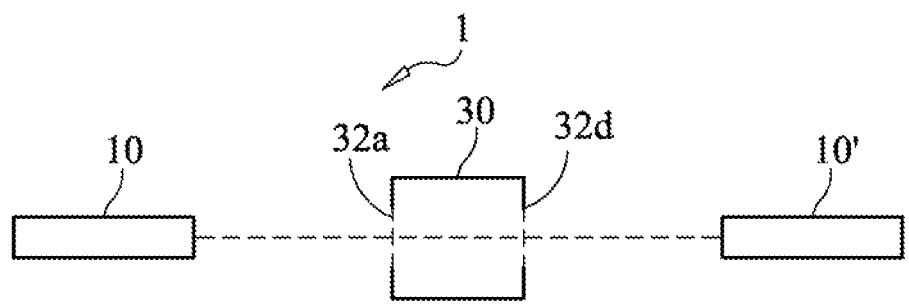
FIG. 1B is a modification of the arrangement shown in FIG. 1A in which an additional device is positioned on a side of the container opposite the device that is also shown in FIG. 1A.

FIG. 1B shows an example wherein a second device 10' is positioned in alignment with device 10, but on the opposite side of container 30 compared to the location of device 10. In this example, container 30 may be entirely acoustically transparent, or contain at least two windows 32a and 32d that are acoustically transparent and that are aligned with the emission pathway of device 10 to permit emissions to pass through both windows 32a and 32d to be received by device 10'. System 1 shown in FIG. 1B, in addition to performing the measurements that the system of FIG. 1A performs, can also measure acoustic properties, including speed of sound and attenuation, which provide indirect measures of tissue microstructure and which may be used for calibration purposes.

According to Torr, "The Acoustic Radiation Force: Am. J. Phys., vol. 52, pp. 402-408, 1984, which is hereby incorporated herein, in its entirety, by reference thereto, acoustic radiation force arises from two sources: "a non zero time-averaged sound pressure in the ultrasonic beam, and the momentum transported by the beam." Torr argues, and it has been widely accepted, that the momentum transfer component of this force dominates under most conditions. This momentum transfer results from attenuation of the propagating ultrasound beam via both absorption and scattering. For the case of total absorption the applied radiation force is simply:

$$F = \frac{W}{c} \quad (1)$$

where W is the acoustic power and c is the speed of sound in the medium. In the case of perfect reflection this radiation force is doubled. In both cases radiation force acts along the direction of wave propagation.

In biological media absorption and reflection are neither total, nor isolated at interfaces. Rather, attenuation and reflection (in the form of scattering) occur throughout volumes of tissue. In these cases radiation force acts as a body force, with the force on a given volume simply equal to the sum of the force from absorption and that from scattering. If we assume that scattering in the tissue consists purely of backscatter, which is of course overly simplistic, then the radiation force applied to a given volume of tissue is:

$$F = \frac{W_a}{c} + \frac{2W_s}{c} \quad (2)$$

where $W_u$ is the absorbed ultrasound power and $W_s$ is the scattered ultrasound power within the volume. If we further simplify by recognizing that only a fraction of the scattered energy is returned as backscatter, and that attenuation is dominated by absorption rather than scattering, then (2) can be simplified as:

$$F = \frac{W_a}{c} = \frac{A}{c} I_o (e^{-2\alpha f x_1} - e^{-2\alpha f x_2}) \quad (3)$$

where A is the cross sectional area of the volume of interest (perpendicular to the axis of propagation), $I_0$ is the ultrasound intensity that would be observed in the absence of attenuation, $\alpha$ is the amplitude attenuation coefficient in Nepers per centimeter per MHz, f is the ultrasonic center frequency in MHz, and $z_1$ and $z_2$ are the ranges of the front and back of the volume in units of centimeters.

By utilizing two devices 10 and 10' (wherein device 10 at least contains an emitter and device 10' contains at least a sensor for receiving the waves/pulses that pass through windows 32a,32d the system can also measure the waves that pass from device 10 to device 10' and estimate acoustic properties of the sample being analyzed. Examples of acoustic properties that may be estimated include attenuation, scattering, and speed of sound during sonorheometry procedures. The data received by device 10' may be used to make predictions/estimations of the applied radiation force and compare experimentally determined displacements to predicted displacements.

Figure 1C:
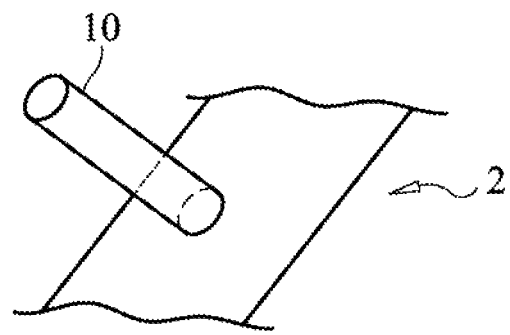
FIG. 1C schematically illustrates a non-invasive use of the present invention.

It should be noted that although FIG. 1A shows an example of apparatus for performing analysis in vitro (such as in a laboratory setting, or from a self-operated testing kit, for example) after taking a sample to be analyzed from a patient and depositing it in container 30, alternatively, the present invention may also be practiced non-invasively, such as by applying acoustic waves from a device 10 transdermally through a patient 2 (in vivo) to the targeted tissue to be analyzed, see FIG. 1C. A single time frame analysis of one or more physical properties of the tissue may be made, or time series studies may be performed by applying the waves transdermally at different time periods, using the techniques described herein for the in vitro studies. Of course the in vivo analyses would typically not involve administration of thrombin or other coagulant to a patient. However time studies may be done to test the effectiveness of an anti-clotting treatment regimen for example. Similarly, time studies may be done to test the effectiveness of a pro-clotting regimen given to a patient to increase the ability of the blood to clot, such as in the case of a hemophiliac, for example. Likewise, the administration of thrombin is not necessarily required for time studies in vitro, as there are other techniques that may be substituted to initiate coagulation, such as snake venom, the use of ground glass to initiate coagulation, etc.

Non-invasive applications of the current invention include characterizing a stage of development of a blood clot by generating a series of acoustic pulses and transdermally directing the series of pulses into the blood such that at least one of the pulses are of sufficiently high intensity to induce physical displacement of the blood, receiving at least two pulses, including at least one pulse reflected from the blood to establish a baseline and another pulse reflected from the blood to estimate at least one characteristic of the physical displacement induced by the waves. Alternatively, the at least two pulses identified above as being used for establishing baseline and estimating a characteristic resulting from the physical displacement of the sample, do not necessarily have to be reflected from the blood/sample. For example, if the sample is contained within membranes that move with the movement of the blood/sample or in a container 30 that is sufficiently flexible (such as a membranous container, for example) to move with the movements of the blood/sample, then the at least two pulses could alternatively be those reflected from the surfaces of the flexible sample container or other membranes placed within the sample, as the movement of the sample (e.g., development of the clot) will alter the position of the surfaces or membranes.

The at least one estimate may be compared to previously generated data to gauge the stage of development of the blood clot being analyzed. The previously generated data may be reference data, such as generated across a larger number of patients and then averaged to determine normal characteristics, as well as to find average levels for characterizing different stages of clotting for example. Optionally, one or more algorithms, techniques or statistical processes may be applied to the at least one estimate to correct for attenuation, scatter and/or other variables before making comparisons to the previously generated data and/or database. Additionally, or alternatively, the prior data or previously generated data may be data generated from one or more previous applications of the present invention to the same patient for the same tissue at prior times. This approach may be used to develop a history, to show the progression of the development of the clot for example. Of course, the in vitro apparatus described herein could be used to carry out the same tests outside of the body, such as in a laboratory or a patient's home test kit.

Still further evaluation of the effectiveness of an anti-clotting treatment may be performed, such as by evaluating the blood prior to application of the treatment by generating a series of acoustic pulses and directing the series of pulses into the blood such that at least one of the pulses is of sufficiently high intensity to induce physical displacement of the blood, receiving at least two pulses reflected from the blood to establish a baseline and to estimate at least one characteristic of the physical displacement induced by the waves, and then repeating these steps at least one time after administration of the treatment Of course, as noted earlier, alternative sensing or receiving steps may be taken to track the movement of the blood, such as by using any of the alternative sensing techniques described above, e.g., laser Doppler, optical coherence tomography, etc. Repealed applications of the steps at predetermined time intervals may be performed if needed to ensure a stabilization of the properties measured, as a result of the treatment. Alternatively, the analysis may indicate that a larger or smaller dose of treatment is needed, or that the treatment is ineffective for a particular patient.

Alternatively, evaluation of the effectiveness of an anti-clotting treatment may be performed by carrying out the analysis steps a number of times after treatment, at predetermined time periods after the administration of the treatment, for example. The results generated from each iteration can then be compared and analyzed to note any changes in the at least one physical characteristic that is being measured/estimated.

Maintenance monitoring can be carried out by the same techniques noted, wherein a patient can be periodically tested to ensure that a clot has not progressed further and/or is dissolving.

Figure 2:
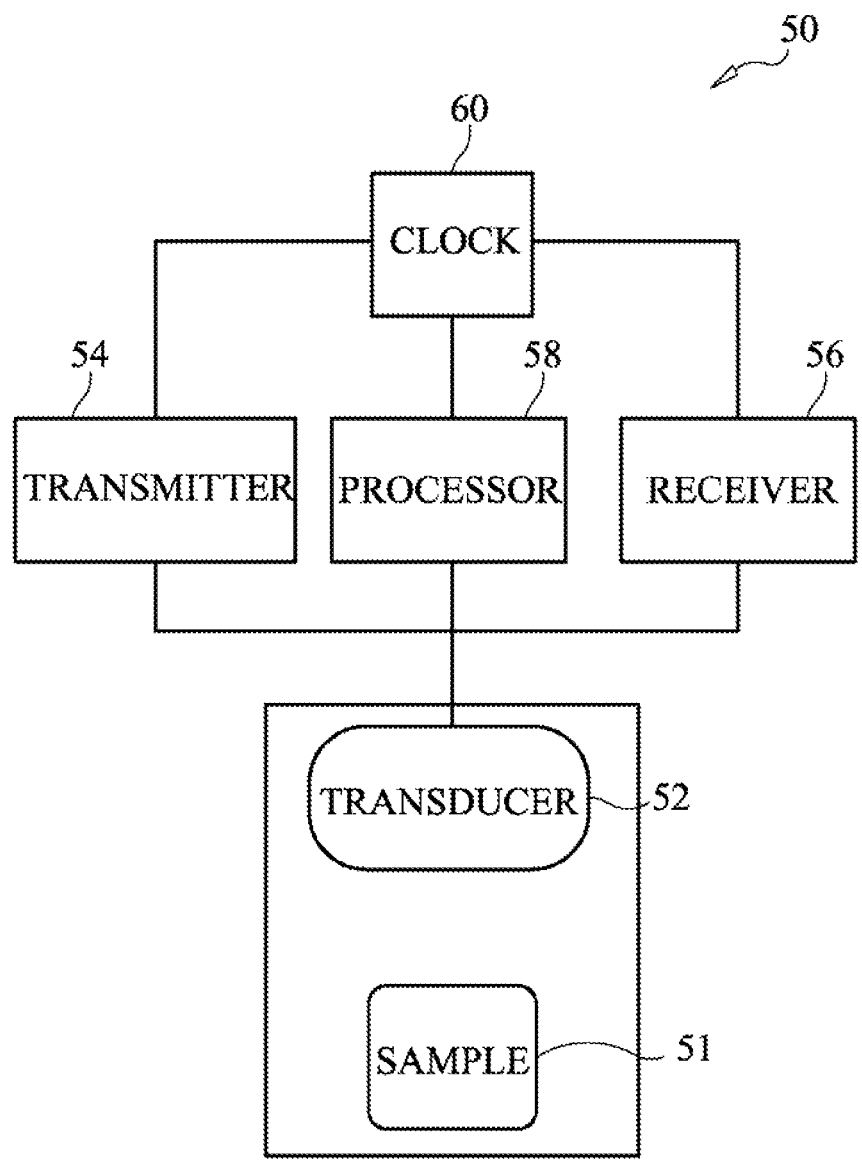
FIG. 2 is a schematic representation of a system for characterization of at lest one physical property of soil tissue.

FIG. 2 shows a schematic representation of an example of a system 50 for characterization of changes in physical properties of soft tissue over time. In this example, a transducer 52, such as may be contained in a device 10 as described above, or directly mounted, fixed to or integral with a container holding a sample 51, for example, is connected to a transmitter 54 as well as receiver 56, both of which are controlled by processor 58 and timed by clock 60.

Clock 60 is provided to control the timing of application of radiation to the sample as generated by transmitter and converted to the acoustic energy at transducer 52, as well as the timing of receiving and interpreting the reflected waves (echoes), by conversion through transducer 52 and receipt of the converted signals at receiver 56, all of which is controlled by one or more processors/microprocessors 58.

Displacements of the soft tissue may be induced by delivering one or more acoustic pulses according to a predetermined frequency through device 10. The displacements may be estimated by applying one or more signal processing algorithms (e.g., minimum sum squared difference motion tracking algorithm, etc.) to the acquired echoes of every nth delivered pulse where "n" is a predefined integer. Alternatively, the signal processing algorithms may be applied to every pulse received. Similarly, algorithms may be applied at every $n^{th}$ time interval for optical waves received. Parameter measurement may be initiated at a predetermined time after one or more coagulation reagents are added to the sample, and such measurements may be repeatedly performed, e.g., once after each passage of a pre-designated time period or according to pre-defined time intervals for measurement. At each acquired time lapse, a time-displacement curve may be generated from which the viscoelastic parameters of the sample can be determined.

Figure 3:
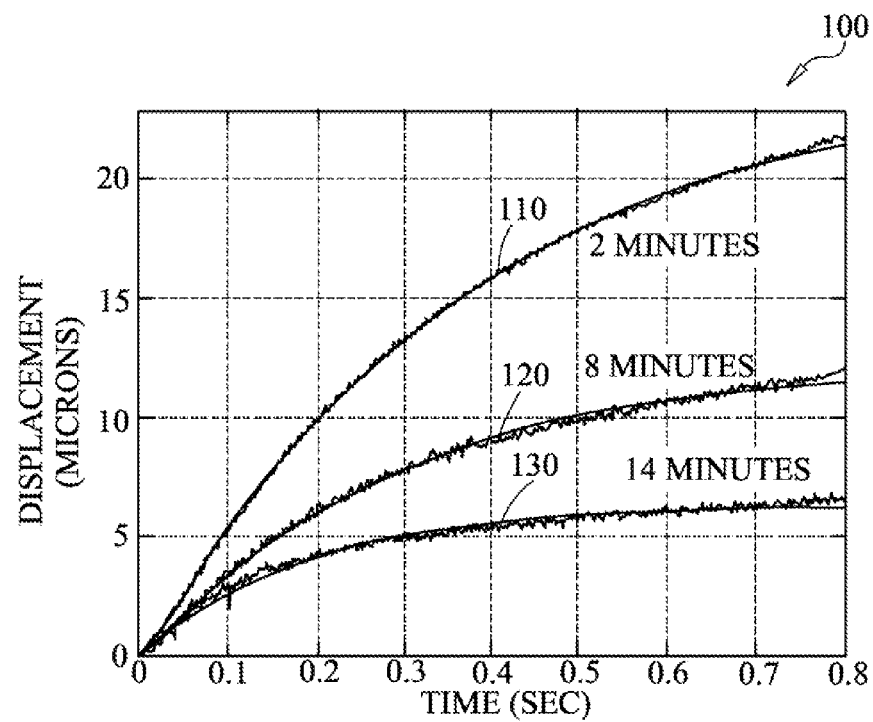
FIG. 3 shows a series of time-displacement curves comparing values predicted by a model to values obtained using an embodiment of the present, apparatus.
Figure 4:
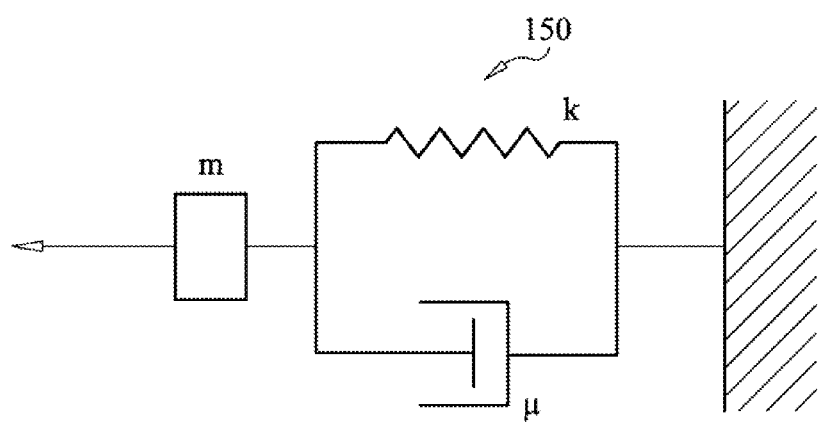
FIG. 4 is a symbolic representation of a modified Voigt model used as a model to characterize the behavior plotted in FIG. 3.

FIG. 3 is a graph 100 showing a set of time-displacement curves 110, 120, 130 obtained during coagulation of a blood sample using the techniques described. Curves 110, 120 and 130 are superimposed on accompanying model predictions, where the mechanical properties of the forming thrombus are modeled by a modified Voigt model 150 as shown in FIG. 4. Experimental results and theoretical predictions show excellent agreement. The basis of the model from which the mechanical parameters are derived is the Voigt model in series with an inertial component.

The modified version 150 of the Voigt model may be used to model the viscoelastic response of blood to acoustic radiation force from which mechanical parameters of the blood may be estimated. Model 150 includes an inertial component "m" in series with the traditional Voigt model, which includes a spring k in parallel with a dashpot μ, as shown in FIG. 4. The governing differential equation for the model is:

$$F(t) = kx(t) + \mu \frac{d}{dt}x(t) + m\frac{d^2}{dt^2}x(t) \quad (4)$$

where F(t) is the applied force as a function of time, x(t) is the induced displacement as a function of time, k is the elastic constant, μ is the viscous constant, and m is the inertial component. System 50 applies radiation force by transmitting a series of pulses to the same location in the blood sample. Assuming that the pulse-to-pulse interval is much shorter than the time constant of the blood's mechanical response, the forcing function may be modeled as a temporal step function as follows:

$$F(t) = Au(t) \quad (5)$$

where A is the force amplitude. Substituting equation (5) into equation (4) and solving for the displacement yields:

$$x(t) = \quad (6)$$

$$\frac{\zeta = \sqrt{\zeta^2-1}}{2\sqrt{\zeta^2-1}} s \square e^{(-\zeta+\sqrt{\zeta^2-1})\omega t} + \frac{\zeta - \sqrt{\zeta^2-1}}{2\sqrt{\zeta^2-1}} s \square e^{(-\zeta-\sqrt{\zeta^2-1})\omega t} + s$$

where ζ is the damping ratio, ω is the natural frequency (in radians per second) and s is the static sensitivity. These parameters are defined as:

$$\zeta = \frac{\mu}{2\sqrt{k \square m}} \quad (7)$$

$$\omega = \sqrt{\frac{k}{m}} \quad (8)$$

$$s = \frac{A}{k} \quad (9)$$

In the examples described herein, the force scaling constant A was not measured. Thus the time-displacement data in this situation can only be used to solve for relative parameters.

To address this limitation, the equations (7), (8) and (9) are redefined according to the following equations (10), (11) and (12) using relative measures of elasticity $k_r$, viscosity $\mu_r$, and mass $m_r$:

$$\zeta = \frac{\mu_r}{2\sqrt{k_r \square m_r}} \quad (10)$$

$$\omega = \sqrt{\frac{k_r}{m_r}} \quad (11)$$

$$s = \frac{1}{k_r} \quad (12)$$

where $k_r = k/A$, $\mu_r = \mu/A$ and $m_r = m/A$.

Although the viscosity, elasticity and inertia are measured as force-dependent parameters, the natural frequency and the damping ratio still remain force-free or force-independent parameters. It is further possible to define a third force-independent parameter, i.e., the time constant $\tau$ as:

$$\tau = \frac{\mu_r}{k_r} \quad (13)$$

The fact that the actual data shown in FIG. 3 waivers or oscillates somewhat about the model data curves suggest that a different model might be used to even more closely model the behavior. In one possible modification, a dashpot would be placed in series with the model shown in FIG. 4. However, the model of FIG. 4 accurately described the response of the blood during formation of a clot with correlation between the data and the model of FIG. 3 being greater that 99% in most of the cases analyzed.

Example

The following example is put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Figure 5:
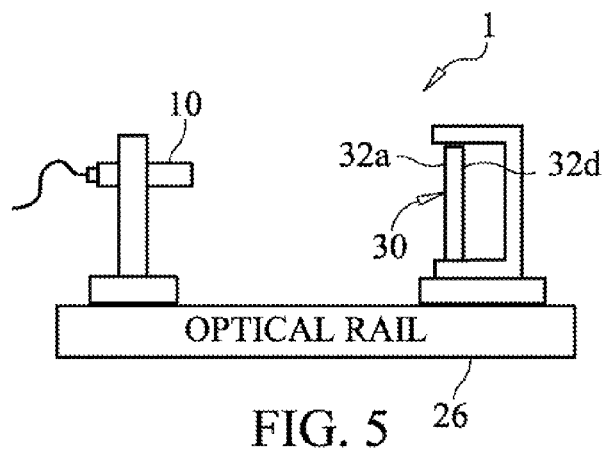
FIG. 5 is a diagrammatic representation of apparatus for in vitro characterization of at least one physical property of soft tissue.

An experimental system 1 as schematically represented in FIG. 5 was used. Device 10 was mounted at one end of a rail and a container 30 was mounted on the opposite end portion of rail 20. Device 10 included a 1.0 cm diameter single piston transducer (General Electric Panametrics V327, Waltham, Mass.) mounted on a five-axis gimbal mount (Newport Corporation, Irvine, Calif.). The transducer had a fixed focus at 4 cm. The transducer was held with the focus at the center of a modified 4.5 mL polystyrene cuvette 30 (Fisher Scientific) that held the blood sample. Cuvette 30 was secured to the rail 20 at a slight tilt so that reflections from the cuvette surface would be directed away from the transducer. Each cuvette 30 was modified by drilling a hole 32a,32d approximately 7 mm in diameter through the front and back sides of cuvette 30 and using silicone sealant (Dow Corning, Baltimore, Md.) to mount a KAPTON® (Dupont, Wilmington, Del.) window over each opening. The KAPTON® windows are acoustically transparent and were provided along the acoustic beam axis of the assembly. The assembly 1 was placed in a water bath held at a room temperature of 21° C.

Transmitted pulses were Gaussian enveloped sinusoids with a center frequency of 10 MHz and a full-width half maximum fractional bandwidth of 75%. The sinusoidal pulses were amplified by 50 dB prior to transmission for a peak-to-peak amplitude of 136 volts. Based on hydrophone measurements performed in the lab, this transmit voltage corresponded to an acoustic intensity ($I_{spta}$) of 300 mW/cm². A series of 4,000 acoustic pulses were transmitted by the transducer at a pulse repetition frequency of 5 kHz to generate acoustic radiation force within the blood. The returning echoes of every tenth transmitted pulse were acquired in order to estimate displacements induced by radiation force. The same digital clock was used to drive pulse generation and data acquisition, reducing sampling jitter to the order of picoseconds.

To confirm the accuracy of these techniques, preliminary experiments were first performed with a control solution. Results obtained from these preliminary experiments were compared to results obtained from use of a conventional rheometer (TA Instruments AR-2000 constant stress rheometer, available from TA Instruments, Wilmington, Del.). An aluminum double-concentric cylindrical geometry was chose for the conventional rheometer because it is best suited for lower viscosity samples that are not sufficiently solid to maintain their structures under a cone and plate or parallel plate setup.

The control solution consisted of a liquid soap (Clean & Clear® Daily Pore Cleanser, Johnson & Johnson) diluted with deionized water. Although a broad variety of solutions were analyzed, including blood mimicking fluids (for flow measurements) and glycerol solutions, the liquid soap solution specified above was bound to offer an appropriate viscoelastic response while remaining homogeneous and stable over time. Further, the spherical "micro-scrubbers" in the soap were excellent ultrasonic scatterers. The control solution consisted of 60% liquid soap diluted with 40% deionized water. A volume of 20 mL of the control solution was prepared, subsequently vortexed, and placed overnight in a vacuum chamber at 20 mmHg to remove air bubbles trapped within the solution.

Approximately 4 mL of the control solution was placed in a 4.5 mL polystyrene cuvette 30 (having been modified as described above) and secured to rail 20 as described above. A sequence of 4,000 pulses was transmitted according to the experimental protocol previously described. A sequence of ten acquisitions was obtained. The solution was gently stirred with a needle between each acquisition to generate a new speckle pattern and avoid settling of the "micro-scrubbers". The remaining 16 mL of solution was used to perform a creep test in the conventional cylindrical rheometer. Displacement data was obtained from an applied shear stress. Because the amount of force applied by acoustic radiation cannot easily be quantified, the maximum displacement observed according to the present techniques (sonorheometry) in the control solution was used to establish the applied shear stress for the creep test on the conventional rheometer. The computer controlling the conventional rheometer was programmed to perform a sequence of ten repeated creep tests for each acquisition obtained with sonorheometry. The temperature control of the conventional rheometer was set to 21° C. to match the temperature of the water bath during sonorheometry experiments.

Following the completion of the control experiments, sonorheometry experiments were performed on blood samples of approximately 4 mL in volume each. Blood was drawn from four healthy volunteers in their mid-twenties and each sample was placed into a modified 4.5 mL polystyrene cuvette 30 having been modified as described above. One of the four test subjects (referred to as "male 2") indicated a recent history of a clotting disorder (deep vein thrombosis). Thrombin (0.5 units per mL of blood) was immediately added to each drawn blood sample in order to induce coagulation. Each combined sample was inverted multiple times to mix the thrombin within the sample. Each cuvette 30 of coagulating blood was mounted to the rail 20 as described above. Sonorheometry experimental protocol was initiated within two minutes of the addition of thrombin. Sonorheometry measurements were repeated over a seventy minute period in order to characterize the blood sample for each respective cuvette 30. Data was acquired every minute for the first ten minutes, every two minutes for the next ten minutes, every three minutes for the next fifteen minutes, and finally, every five minutes for the next thirty-five minutes for a total of twenty-six acquisitions per sample.

The sum squared differences (SSD) algorithm was applied between the first and the $n^{th}$ echoes (where n is a predefined integer that defines how often echoes or waves are considered to estimate a tissue displacement measurement; in this example, n was set to 10) to determine the tissue displacement at a given range, see Viola et al., "A Comparison of the Performance of Time Delay Estimators in Medical Ultrasound", IEEE Transactions on Ultrasonics, Ferroelectrics, and Frequency Control, vol. 50, no. 4, pp. 392-401, 2003, which is incorporated herein, in its entirety, by reference thereto. Sub-sample delays were estimated by identifying the location of the peak of a parabolic fit about the minimum of the SSD grid. The ensemble of these displacement estimates form a time-displacement curve that holds combined information about both elastic and viscous components of the blood sample being analyzed.

In order to model the viscoelastic response of coagulating blood to thus estimate the mechanical parameters, the modified version of the Vogt model (described above with regard to FIG. 4) was applied to the experimental data acquired. The governing differential equation for this application is equation (1) above. Device 10 of system 1 applied radiation force by transmitting a series of 4,000 ultrasonic pulses to the same location within the blood sample.

Figure 6A:
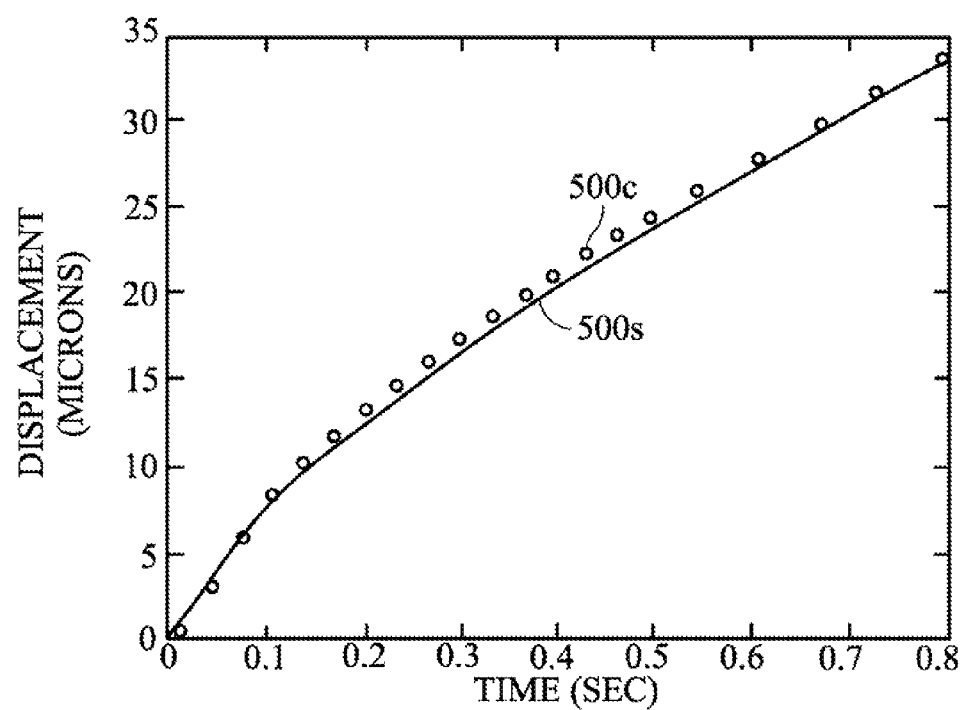
FIGS. 6A, 6B and 6C show a portion of the results obtained from analyzing a control solution as described in the Example below.
Figure 6B:
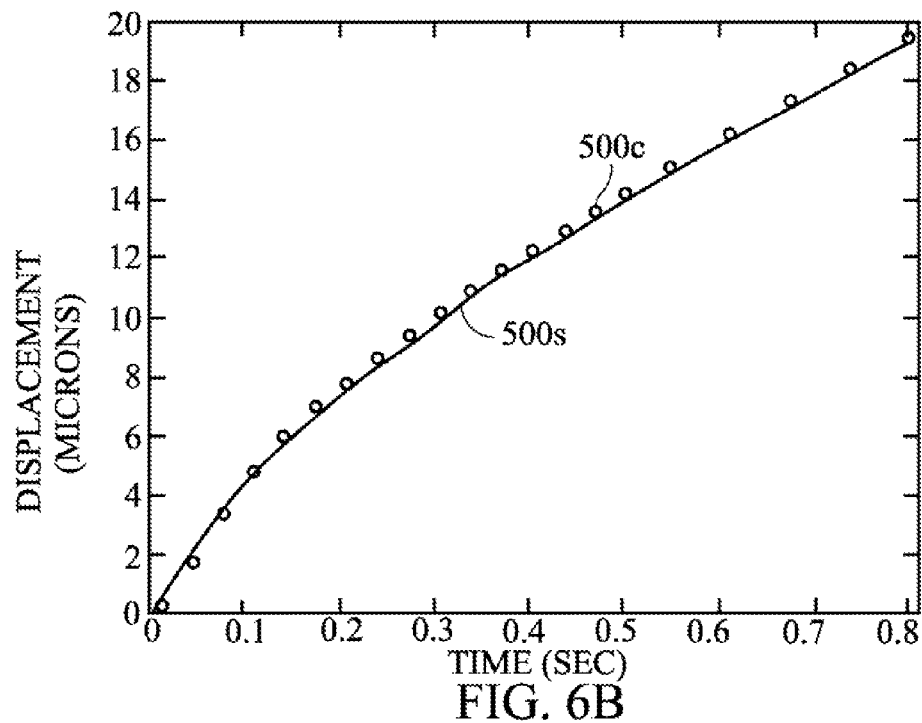
Figure 6C:
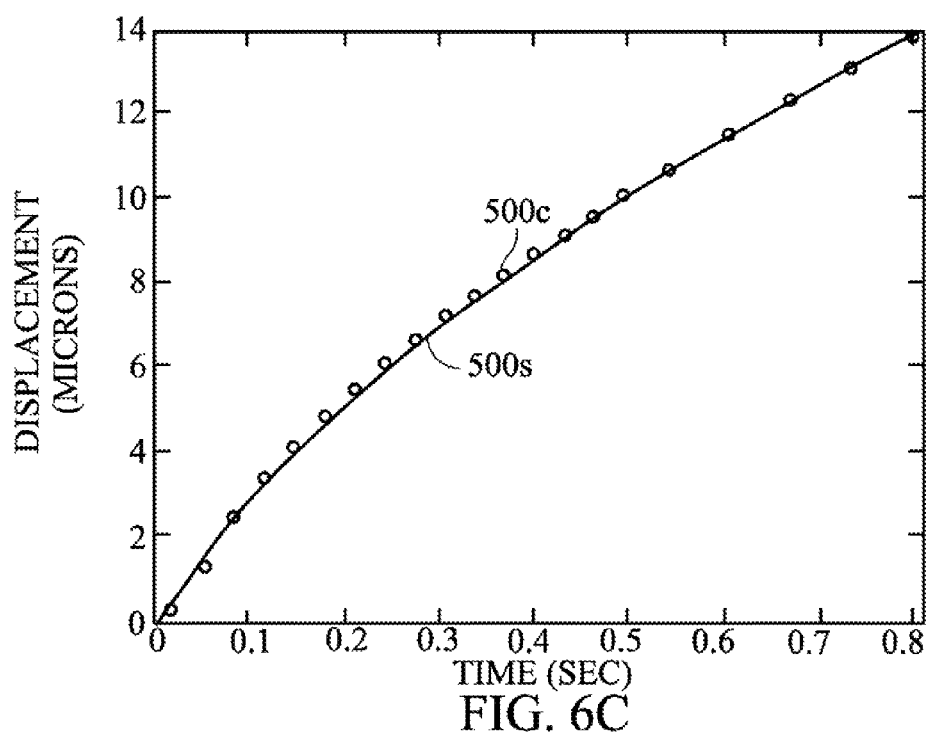

A portion of the results obtained from analyzing the control solution is shown in FIGS. 6A-6C. Of one hundred paired time-displacement curves, each overlaying a curve obtained via sonorheometry over a corresponding curve obtained with the convention cylindrical rheometer, three such curves are shown, see FIGS. 6A-6C, respectively. The sonorheometry data is presented as a continuous line 500*s*, while the conventional cylindrical rheometer data is displayed by circles 500*c*. Similar results to those shown were obtained for the remainder of the control experiments. The correlation coefficient between the data obtained by the two methods ranged from 0.9990 to 0.9999, with an overall mean correlation coefficient of 0.9993.

Figure 7:
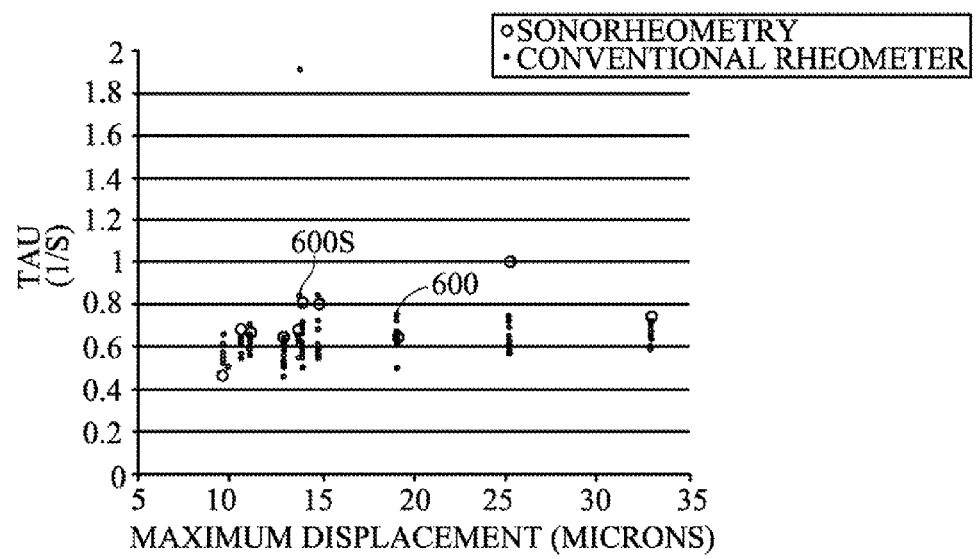
FIG. 7 shows comparative time constants for convention rheometry uses as compared to use of the present techniques.

FIG. 7 shows estimated time constants (i.e., "tau" or "τ") as a function of maximum achieved displacement. Black circles 600*s* represent the time constants estimated from the present methods (sonorheometry) while gray diamonds 600*c* represent the estimates from the conventional rheometer. The time constants, as shown, have values ranging from approximately 0.45 to 1.91 seconds, while the majority of the time constants lie around 0.6 seconds.

Figure 8:
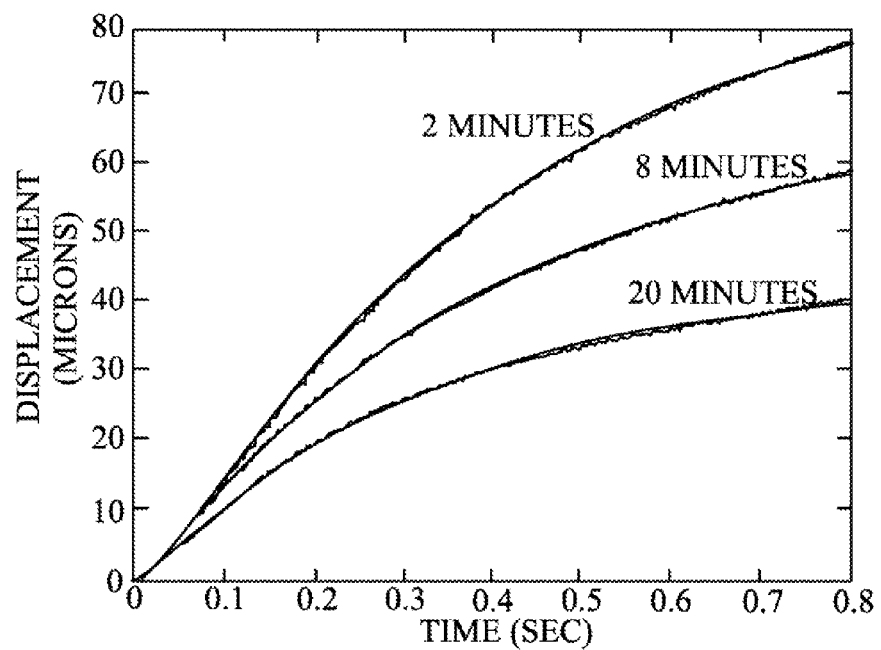
FIG. 8 shows a set of time-displacement curves obtained from one blood sample along with the accompanying best fit model predictions, as described below in the Example.

FIG. 8 shows a set of time-displacement curves obtained from one blood sample along with the accompanying best fit model predictions. The predictions are the smooth lines and the time displacement curves generated from the experimental data are the slightly wavering lines. The displayed curves indicate displacement at the same axial location with cuvette 30 for a single sample taken from female subject 2. Although coagulation data was acquired at twenty-six time intervals in the seventy minute experimental period, for sake of simplicity, only the experimental curves obtained at two, eight and twenty minutes have been displayed. Similar curves were obtained for the other acquisition times. Experimental results and best fit models show excellent agreement. The peak-to-peak error in displacement estimates was on the order of 0.5 microns.

Maximum detected displacement of the blood samples progressively decreased as a blood clot started to form in each respective cuvette 30. After a certain amount of time, which was unique to each subject, no appreciable displacement could be detected. The results also suggested that the axial position from which displacements were detected became progressively narrower with the passage of time.

The estimated (calculated) relative modulus of elasticity and relative viscosity values clearly showed that the relative modulus of elasticity increased as the clot formed, and this was consistent for all four subjects tested. As to viscosity, the two female subjects showed increasing relative viscosity as the clots were forming, while for the male subjects, relative viscosity remained fairly constant, with some increase near the conclusion of coagulation.

As to force-free (force independent parameters), the time constant, expressed in seconds, decreased with time for all four subjects, which was expected since the blood becomes stiffer as time elapses. For example, the time constant of the "female 1" subject decreased from about 0.6 seconds at the two minute test time to a value of about 0.3 seconds at the twenty minute test time, and the time constant of the "male 2" subject had a value of 0.45 seconds at the two minute test time and decreased to 0.2 seconds at the sixteen minute test time. Similar trends were observed for damping ratios, where clotting blood exhibits lower values. As expected, blood samples are always over-damped systems. In contrast with the other two force-free parameters examined, natural frequency increases as blood is coagulating, reaching values of about 500 rad/sec (for female 1 and female 2).

That which is claimed is:

1. A method of characterizing changes in at least one physical property of a biological material over time, said method comprising:

providing a generator capable of generating a series of acoustic pulses;

generating a series of acoustic pulses using the generator and directing said series of pulses into the biological material such that at least one of the pulses is of sufficiently high intensity to induce physical displacement of the biological material, wherein each of said acoustic pulses is of finite duration and of brief duration relative to a duration of said generating and said directing;

estimating at least one physical property of the biological material based on measuring a displacement resulting from said induced physical displacement of the biological material; and repeating said generating and estimating steps after passage of a time interval.

2. The method of claim 1, wherein said estimating is based on receiving at least two of said acoustic pulses reflected from the biological material and estimating the at least one physical property based on the acoustic pulses received.

3. The method of claim 1, wherein said estimating is based on receiving optical reflections from the biological material as the biological material is being physically displaced and estimating the at least one physical property based on the optical reflections received.

4. The method of claim 1, wherein said generating and estimating steps are repeated after passage of each of a plurality of predetermined time intervals.

5. The method of claim 1, further comprising outputting at least one measured characteristic from each performance of said generating and measuring steps.

6. The method of claim 5, wherein said outputting comprises plotting time-displacement data.

7. The method of claim 1, wherein the biological material is blood.

8. The method of claim 7, further comprising calculating a rate of fibrinolysis of the blood, based upon at least a portion of a time series of said at least one characteristic resultant from said generating and measuring steps.

9. The method of claim 7, further comprising calculating progress of hemostasis of the blood, based upon at least a portion of a time series of said at least one characteristic resultant from said generating and measuring steps.

10. The method of claim 1, wherein said at least one physical property comprises at least one parameter determined by fitting experimental data including a plurality of said estimates or measurements, to a theoretical model defining the at least one characteristic.

11. The method of claim 10, wherein said at least one physical property comprises at least one of relative viscosity and relative elasticity of the biological material.

12. The method of claim 1, wherein said at least one physical property comprises at least one of relative viscosity and relative elasticity of the biological material.

13. The method of claim 1, wherein said at least one physical property comprises at least one force-free parameter.

14. The method of claim 1, wherein said acoustic pulses are ultrasound pulses.

15. The method of claim 7, further comprising calculating a characteristic of coagulation of the blood, based upon at least a portion of a time series of said at least one physical property resultant from said generating and measuring steps.

16. The method of claim 15, wherein said characteristic comprises a rate.

17. The method of claim 15, wherein said characteristic comprises a clot stiffness.

18. The method of claim 15, wherein said characteristic comprises a time to clot.

19. The method of claim 15, wherein said characteristic comprises a time to clot dissolution.

20. The method of claim 7, further comprising identifying a stage of development of a blood clot in the blood, based upon at least a portion of a time series of said at least one characteristic resultant from said generating and measuring steps.

21. The method of claim 1 performed on a patient.

22. The method of claim 21, wherein the biological material is blood.

23. The method of claim 1, further comprising receiving at least a portion of said pulses that pass through the biological material and estimating at least one acoustic property of the biological material.

24. The method of claim 23, wherein said pulses that pass through the biological material are received on an opposite side of the biological material from a side where said pulses enter the biological material.

25. The method of claim 23, wherein said at least one acoustic property comprises at least one of attenuation and speed of sound.

26. The method of claim 23, further comprising estimating a magnitude of applied force of the at least one pulse having sufficiently high intensity to induce physical displacement of the biological material, based upon said at least one estimated acoustic property.

27. The method of claim 1, wherein the biological material comprises soft tissue.

28. The method of claim 1, wherein the biological material comprises blood.

29. The method of claim 1, comprising placing the biological material in contact with a control material, and controlling the temperature of the control material.

30. The method of claim 1 performed non-invasively on a patient.

31. A method of characterizing changes in at least one physical property of a material over time, said method comprising:
    providing a generator capable of generating a series of acoustic pulses;
    applying a device to an animal body comprising the material;
    generating a series of acoustic pulses using the generator and directing said series of pulses into the material such that at least one of the pulses is of sufficiently high intensity to induce physical displacement of the material, wherein each of said acoustic pulses is of finite duration and of brief duration relative to a duration of said generating and said directing;
    estimating at least one physical property of the material based on measuring a displacement resulting from said induced physical displacement of the material; and
    repeating said generating and estimating steps after passage of a time interval.

32. The method of claim 31, wherein said applying a device comprises inserting at least a portion of the device invasively within the body.

33. The method of claim 31, wherein the material comprises soft tissue.

34. The method of claim 31, wherein the material comprises blood.

35. The method of claim 1, wherein said at least one physical property comprises viscosity of the biological material.

36. The method of claim 1, wherein said at least one physical property comprises elasticity of the biological material.

37. The method of claim 1, wherein said at least one physical property comprises a combination of shear and compressive modulus of the biological material.

* * * * *